(12) United States Patent
Shepard et al.

(10) Patent No.: US 8,852,892 B2
(45) Date of Patent: Oct. 7, 2014

(54) PHYSICAL GEOLOCATION SYSTEM

(75) Inventors: Donald F. Shepard, Evergreen, CO (US); David B. Knaebel, Manlius, NY (US); D. Anthony Gray, Liverpool, NY (US)

(73) Assignee: Syracuse University, Syracuse, NY (US)

( * ) Notice: Subject to any disclaimer, the term of this patent is extended or adjusted under 35 U.S.C. 154(b) by 480 days.

(21) Appl. No.: 12/701,318

(22) Filed: Feb. 5, 2010

(65) Prior Publication Data

US 2010/0138164 A1 Jun. 3, 2010

Related U.S. Application Data

(62) Division of application No. 10/983,379, filed on Nov. 8, 2004, now abandoned.

(60) Provisional application No. 60/518,109, filed on Nov. 7, 2003.

(51) Int. Cl.
*C12P 19/34* (2006.01)
*G06F 19/00* (2011.01)

(52) U.S. Cl.
CPC .......... *G06F 19/3493* (2013.01); *G06F 19/366* (2013.01)
USPC ...................................... 435/91.2

(58) Field of Classification Search
USPC ................................ 435/91.2, 6.1
See application file for complete search history.

(56) References Cited

U.S. PATENT DOCUMENTS

| | | | | |
|---|---|---|---|---|
| 5,210,015 A | * | 5/1993 | Gelfand et al. | 435/6.11 |
| 5,501,080 A | * | 3/1996 | McManus et al. | 62/55.5 |
| 5,766,953 A | * | 6/1998 | Kennedy | 436/31 |
| 6,016,713 A | | 1/2000 | Hale | |
| 6,101,886 A | | 8/2000 | Brenizer et al. | |
| 6,122,396 A | * | 9/2000 | King et al. | 382/133 |
| 7,217,510 B2 | | 5/2007 | Ecker et al. | |
| 2002/0124664 A1 | * | 9/2002 | Call et al. | 73/863.22 |
| 2009/0000188 A1 | * | 1/2009 | Sayers et al. | 47/58.1 R |
| 2010/0196881 A1 | * | 8/2010 | Callison et al. | 435/6 |
| 2010/0332474 A1 | * | 12/2010 | Birdwell et al. | 707/737 |

FOREIGN PATENT DOCUMENTS

WO    WO 9824929 A1 * 6/1998

OTHER PUBLICATIONS

Rolf, et al., Polymorphism at the tetranucleotide repeat locus DYS389 in 10 populations reveals strong geographic clustering, Eur J of Hum Gen (1998) 6, 583-588.

* cited by examiner

*Primary Examiner* — Cynthia B Wilder
(74) *Attorney, Agent, or Firm* — George R. McGuire; Frederick J. M. Price; Bond Schoeneck & King, PLLC

(57) ABSTRACT

A real-time system for determining the geographic movements of an individual or object by sampling particulates contained thereon. The system includes particle collection, sample preparations, and sample analysis using three primary modes of detecting certain particulates. The first mode involves the imaging of pollen, spores, or other biological material which are visible through a light microscope when properly stained or prepared. The second mode involves the use of real-time polymerase chain reaction to amplify and detect target nucleic acid sequences. The third mode involves the use of X-ray diffraction to identify mineral particles. The results from any mode, or any combination of modes, are analyzed by comparison to a reference database containing geographic information and the results are compiled by a controller for visual display.

12 Claims, 3 Drawing Sheets

PHYSICAL GEOLOCATION SYSTEM

CROSS-REFERENCE TO RELATED APPLICATION

This present application is a divisional of and claims priority to U.S. patent application Ser. No. 10/983,379, filed on Nov. 8, 2004 and now abandoned, which claims priority to U.S. Provisional Application Ser. No. 60/518,109, filed on Nov. 7, 2003 and entitled "Physical Geolocation System."

BACKGROUND OF THE INVENTION

1. Field of Invention

The present invention relates to the verification of geographic location information and, more specifically, to a system for determining the geographic travel history of an object or individual based on an analysis of particulates contained thereon.

2. Description of Prior Art

As worldwide commerce and travel continues to expand, there is an increased need to determine the geographic travel history of an individual or object that crosses geographic, political, or national borders. Determining the international transit of persons and/or objects can be important for the purposes of maintaining security, insuring the safety of food shipments and agricultural products, or merely verifying the authenticity of travel documents and shipping records.

Conventional particulate analysis involves the manual collection of particulates and analysis by skilled technicians using a light microscope of other analytical techniques. This process requires days to implement and results in the distribution of outdated information.

3. Objects and Advantages

It is a principal object and advantage of the present invention to provide a system for determining the geographic travel history of an individual or object that uses objective measurements.

It is an additional object and advantage of the present invention to provide a system for determining the geographic travel history of an individual or object that relies on stable and tenacious data sources.

It is a further object and advantage of the present invention to provide a system for determining the geographic travel history of an individual or object that relies on data sources that are otherwise unnoticed.

Other objects and advantages of the present invention will in part be obvious, and in part appear hereinafter.

SUMMARY OF THE INVENTION

The present invention is a geographic location system comprising the collection of microscopic particulates deposited on or entrapped in an individual or object when moving through a geographic region and the analysis of the microscopic particulates to determine which geographic regions the individual or object has contacted. The microscopic particulates can comprise pollen, fungal spores, soil/clay minerals, or DNA-bearing organisms that vary based on geographic locale. These particulates are generally distributed in the atmosphere, stable, and readily adhere to individuals or objects. As different regions produce varying pollens, spores, and minerals, geographic information about an individual or object may be gleaned from the particular types of particulates. Additionally, as pollen and spore types can vary seasonally, temporal information may also be extracted from an analysis of embedded particulates to build a comprehensive travel history.

The geographical location system comprises the use of some or all of a series of operative modules: a particle collection module, a sample preparation module, an image analysis module, a DNA analysis module, an X-ray diffraction (XRD) module, a controller module, and a database module. One, two, or all three of the analytical modules can be used to achieve geolocation. The data extracted from these various modules is compared against a Physical Geolocation System database having pollen/spore images, DNA sequences, and XRD spacing for various particles, as well as information on geographic distribution necessary for developing a travel history.

The particle collection module comprises a high volume air sampler that generates an aqueous suspension of collected particles in a given air sample. The air sample can be ambient air, air in a confined space (such as a shipping container, tractor trailer, or piece of luggage), or air passed over a person or object. Instead of an air sampler, the particle collection module may comprise the use of a sterile swab or implement to collect particulates from the surface of an object or person. The particles from the swab may then be placed in an aqueous solution for further processing.

The liquid sample generated by the particle collection module is passed to the sample preparation module, which divides the sample into sub-samples and treats it for analysis by the various analysis modules. For example, a sub-sample destined for image analysis will be treated with dyes, a sub-sample destined for DNA analysis will be purified and have target DNA isolated. One sub-sample may be archived for later analysis or re-analysis if necessary.

The image analysis module comprises an automatic microscope system including a microscope, automatic motorized stage, charged-coupled device (CCD) camera, and controller. The image analysis module automatically acquires images of pollen and spores for comparison to the image database. The image analysis module passes pollen and/or spore identification to the controller.

The DNA analysis module comprises a real-time polymerase chain reaction (PCR) system for evaluation of the sample through rational PCR primer and probe combinations that target 18S ribosomal genes or other discriminatory genes. Other DNA analytical approaches (e.g., real time Terminal Restriction Fragment Length Polymorphism (TRFLP) analysis) may be incorporated as they become available. The DNA analysis module passes plant/fungi identification information to the controller.

The XRD module comprises a commercial off-the-shelf (COTS) scanning XRD device for providing rapid, high-definition diffraction spacings of the sample. The spacings are compared to a source database to determine mineral composition and then screened against worldwide soil mineralogy databases. The XRD module passes soil identification to the controller module.

The controller module coordinates, collects, interprets, and displays the information provided by the forgoing modules. The information may be displayed as a map of areas consistent with the analyses, as well as text describing the types of pollen, spores, and minerals and statistical confidence values.

DETAILED DESCRIPTION

Figure 1:
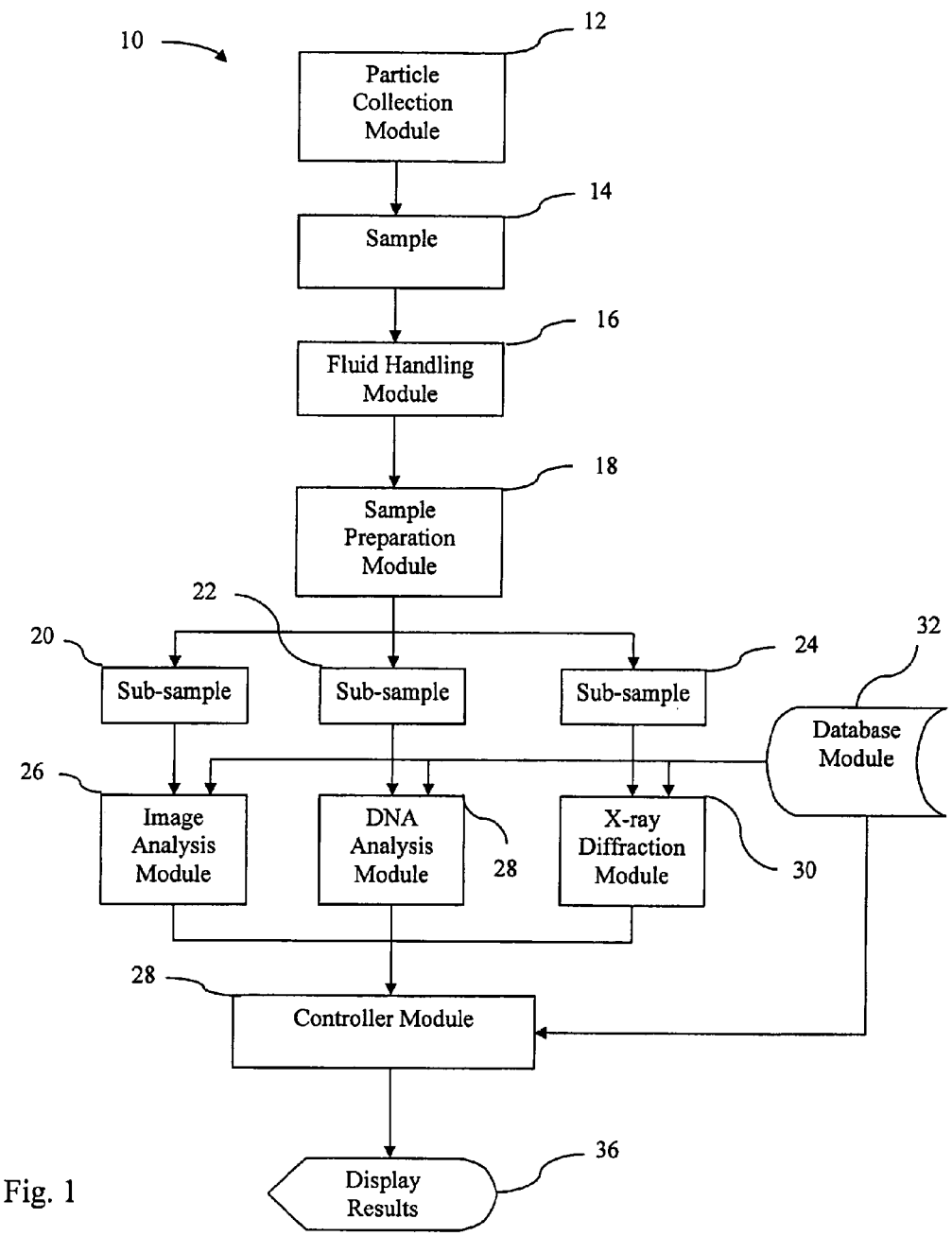
FIG. 1 is a schematic diagram of a physical geolocation system according to the present invention.

Referring now to the figures, wherein like numerals refer to like parts throughout, there is seen in FIG. 1 a physical geolocation system 10 according to the present invention for rapidly collecting and analyzing particulates collected from a person or object. System 10 comprises a particle collection module 12 for physically collecting particles from a target individual or object, such as a shipping container, piece of luggage, or agricultural product. Particle collection module 12 includes a high volume air sampler for generating an aqueous suspension of collected particles from a given air sample. The air sample taken can be ambient air, air in a confined space (such as a shipping container, tractor trailer, or piece of luggage), or air passed over a person or object. Acceptable samplers include the SpinCon of Sceptor Industries and the M-Vac of Rocky Mountain Labs. Particle collection module 12 may also comprise a sterile swab or implement for collecting the particulates from the surface of a person or object. The particles from the swab may then be placed in an aqueous solution for further processing according to the present invention.

The liquid sample 14 generated by particle collection module 12 is then preferably distributed robotically by a fluid handling module 16 to a sample preparation module 18 for ensuring sample integrity and minimizing cross-contamination. A Gilson Multiple Probe 215 Liquid Handler may serve as fluid handling module 16.

Sample preparation module 18 is responsible for preparing sample 14 for each of the primary forms of analysis used to screen for particles having biological and geological (i.e., soil) significance. Liquid sample 14 is separated by sample preparation module 18 into sub-samples 20, 22, and 24 for individual analysis by an image analysis module 26, a DNA analysis module 28, and an XRD module 30. For example, sub-sample 20 is treated with dyes to enhance imaging, sub-sample 22 is treated to isolate and purify and DNA contained therein, and sub-sample 24 is prepared for x-ray diffraction.

Additional sub-samples (not shown) may be archived for delayed analysis or analysis by other methods, or even for re-analysis if necessary. To eliminate cross-sample contamination, system 10 handles all samples and sub-sample as discrete units; all sample collection and processing is done via robotic transfer of these discrete units, and all modules maintain sample integrity. An acceptable sample preparation module 18 is the Cyberlab C-400 system, manufactured by Gilson, Inc. of Middleton, Wis.

After treatment with appropriate dyes, sub-sample 20 is provided to image analysis module 26. Image analysis module 26 comprises a conventional microscope having an automatic motorized stage for accepting sample 14 and an attached CCD camera for recording images. Image analysis module 26 may comprise another type of platform that does not depend on motorized stages or conventional microscope architectures as long as the microscope is capable of automated image acquisition. Image analysis module 26 automatically acquires images of stained pollen and spores in sample 14 for comparison to a database 32 containing previously identified pollen and spore images and data. Once an identification is made by cross-checking the image of sub-sample 26 with images stored in database 32, image analysis module 26 communicates the pollen/spore identification information to a controller module 34. Image information for database 32 may be obtained or collected from pollen image databases such as PalDat of the Department of Ultrastructure Research and Palynology, University of Vienna, Austria, or several other known databases.

After isolation and purification of DNA in sub-sample 22 by sample preparation module 18, DNA analysis module 28 performs real-time polymerase chain (PCR) using rational PCR primer and probe combinations that target 18S ribosomal genes or other discriminatory genes (or another analytical approach such as TRFLP) to identify the presence of particular pollen and/or spore DNA identification in sub-sample 34. DNA analysis module 60 identifies the type of pollen and spores present in sub-sample 34 by comparing the results of PCR with plant DNA sequence data stored in database 32, and then communicates the identity information to controller module 34. A MacConnell Mini Prep system from MacConnell Research Corp., San Diego, Calif. may provide DNA extraction and preparation for DNA analysis module 60. The Chromo 4 system from MJ Research, Waltham, Mass., may serve as real-time DNA analysis module 28. Genetic information for database 36 may be compiled from gene sequence resources such as GenBank, the National Institutes of Health (NIH) genetic sequence database and the Ribosomal Database Project (RDP) of Michigan State University.

Sub-sample 24 is provided to an XRD analysis module 30 comprising a COTS scanning XRD device. XRD analysis module 30 device provides rapid, high-definition diffraction spacings of mineral in sub-sample 24 for comparison to known mineral spacings stored in database 32 to determine mineral composition and geographic information. XRD analysis module 30 provides mineral identification and geographic information to controller module 34. A Bede D1 diffraction system from Bede Scientific Inc., Englewood, Colo. may be used as XRD analysis module 30. XRD information for database 36 may be obtained or collected from the International Centre for Diffraction Data database.

Figure 2:
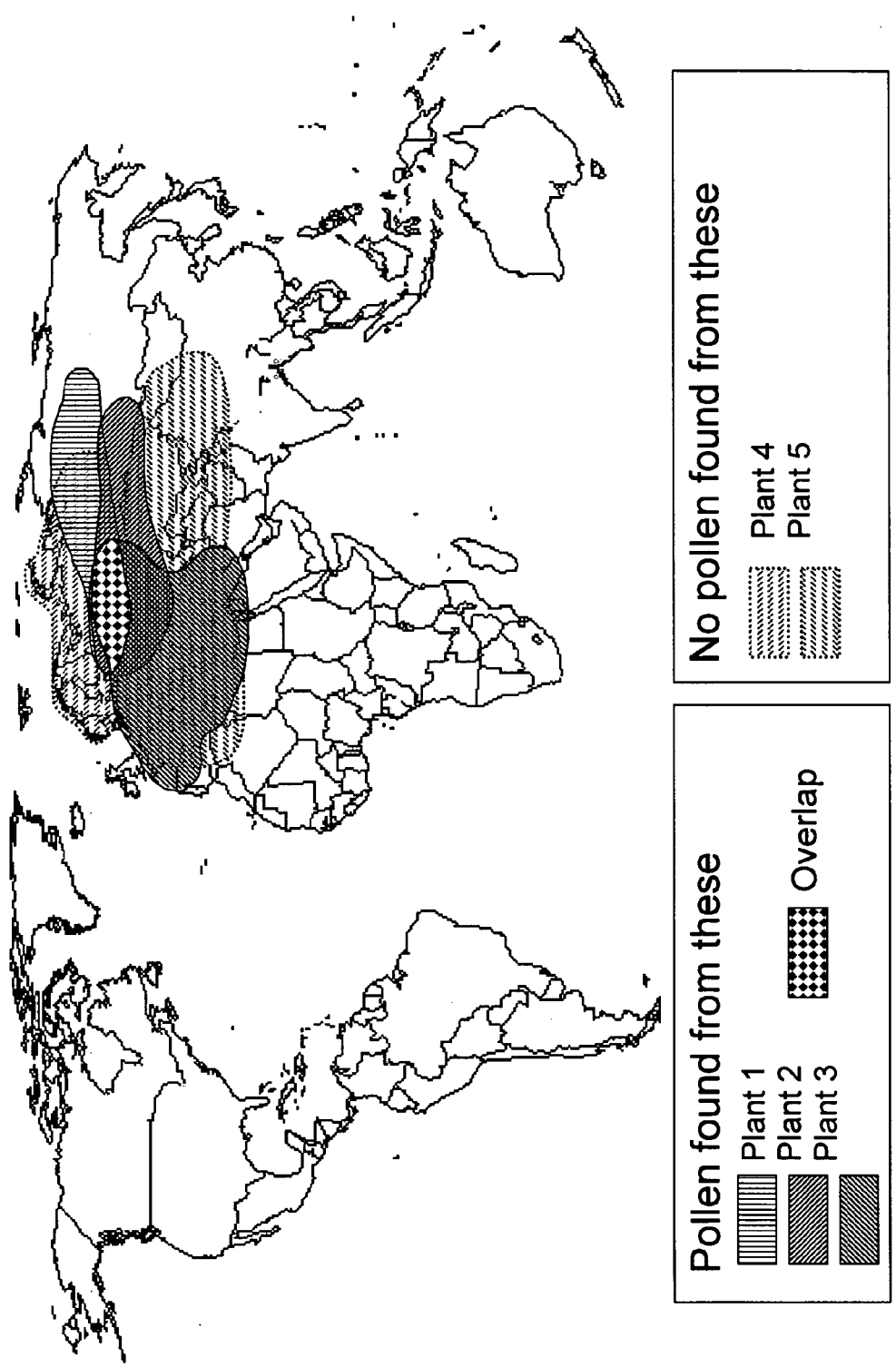
FIG. 2 is an illustration of a physical geolocation system display according to the present invention.
Figure 3:
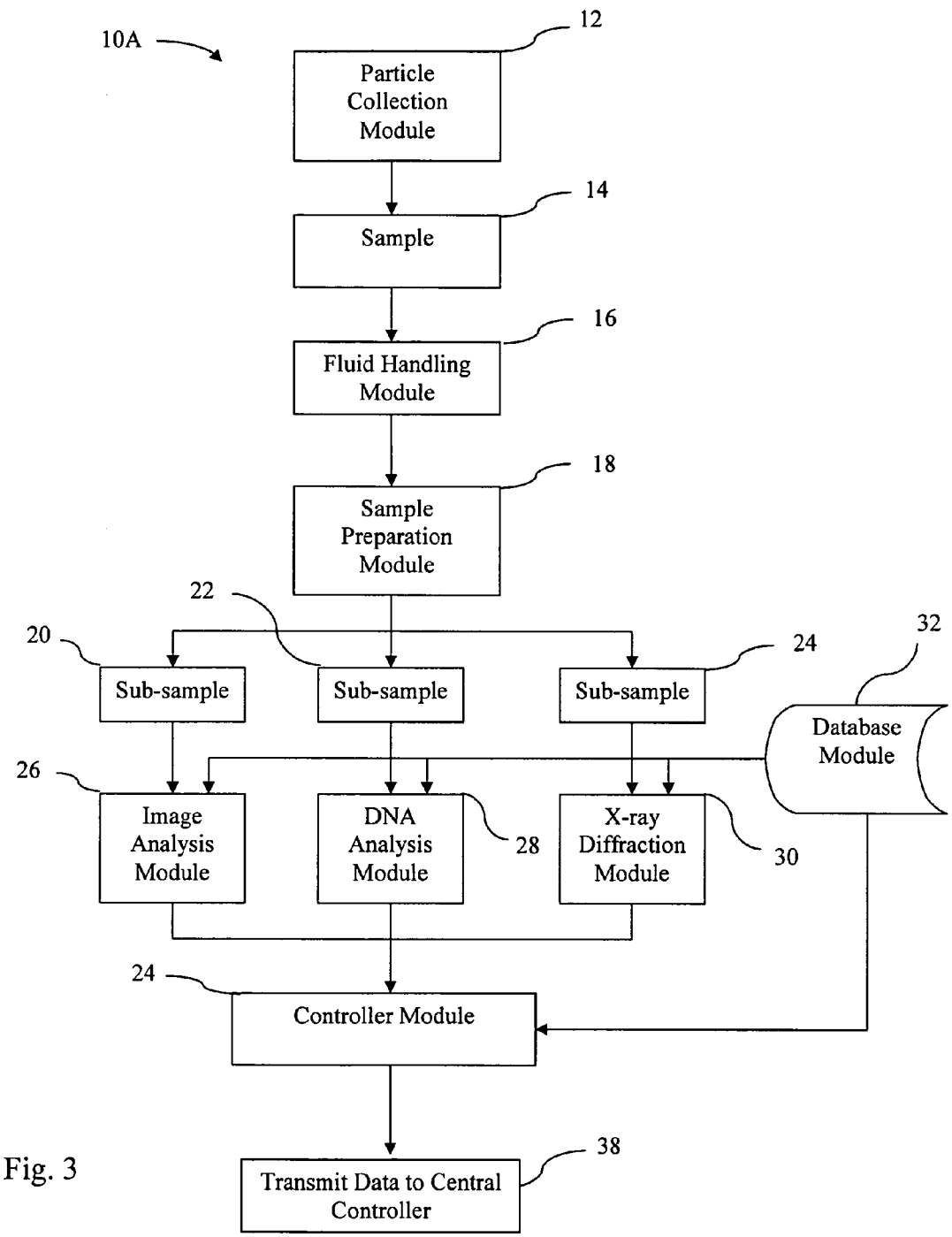
FIG. 3 is a schematic diagram of a real-time monitoring system according to the present invention.

Controller module 34 coordinates, collects, and interprets the information provided by image analysis module 26, DNA analysis module 28, XRD module 30, and database module 32. Using the identity information provided by image analysis module 26, DNA analysis module 28, XRD analysis module 30, and data stored in database module 32, controller 34 can compile geographic locations from the known geographic territories for identified particulates for visual display 36. As seen in FIG. 2, information derived by the foregoing modules that is collected and interpreted by controller module 34 may be displayed by mapping an area that is consistent with the analyses, as well as providing text that describes the types of pollen, spores, and minerals with appropriate statistical confidence values.

Physical geolocation system 10 may be used in a host of agricultural applications. For example, physical geolocation system 10 can determine the probable country of origin for imported fruits and vegetables, thereby determining treatment under the North American Free Trade Agreement (NAFTA). By determining the probable country of origin, officials will also be able to determine if the agricultural items must be quarantined or even destroyed, based on their knowledge of agricultural problems in other countries. For example, physical geolocation system 10 can be used to screen agricultural products that originate from a geographic region having food-related medical problems, such as hoof-and-mouth disease.

Physical geolocation system 10 may also be used to interrogate individuals as they enter a country. By compiling a real-time travel history, customs officials can make security decisions based on objective information about the recent whereabouts of a suspicious person, rather than relying on subject measures, such as racial profiling.

Physical geolocation system 10 may be modified to serve as a real-time monitoring system 10A, for providing real-time agricultural data to scientists and the public, or real-time allergen analysis to scientists and the public. Operation of real-time monitoring system 10A is similar to physical geolocation system 10, except that database 32 contains records of pollens, spores, bacteria, allergenic compounds, and potential pathogens having agricultural, biological, or health significance, rather than geographic territories. By cross-checking samples against the modified database, pollen and spores from neighboring geographic locations, known allergens, pollen or DNA from invasive or pest plant species, or spores associated with pathogenic fungal species can be detected, identified and reported.

A network of real-time monitoring systems 10A that communicate with or transmit data to a central controller 38 can identify the presence of a potential plant or livestock disease outbreak or provide an early warning to the proper authorities. A network of real-time monitoring systems 10A deployed across a geographic or agricultural region also permits the real-time sampling, identification, and reporting of airborne agricultural pathogens, including intentionally released organisms in the event of a bio-terrorism event. The advanced warning of a possible outbreak provided by a network of real-time monitoring systems 10A allows enhanced planning to more effectively treat potentially affected crops or livestock.

Real-time monitoring systems 10A may also provide early warning of weed or other undesirable plant infestations. By determining changes in the distribution of pollens identified from a network of real-time monitoring systems 10A, the future density and distribution of unwanted plant species can be estimated and consulted when making eradication and/or control decisions.

Real-time monitoring systems 10A may also provide real-time allergen data to allergy suffers. For allergy applications, samples of ambient air are taken and digital images, DNA sequences, and XRD data of the particulate content are identified and crosschecked against available pollen and fungal spore allergen morphology, pollen and spore DNA databases, and diffraction data stored in database 32. Identified allergens are reported along with a measure of their concentration (frequency of occurrence). Real-time analysis of allergens will allow the healthcare community to more readily associate allergens with symptoms and offer targeted treatments.

What is claimed is:

1. A method of determining the geographic history of a target, comprising the steps of:
    collecting a sample of pollen particles from said target by a sample collection module, wherein said step of collecting a sample of particles from said target comprises taking a high volume air sample and forming an aqueous suspension of said particles;
    identifying at least one pollen particle in said sample by at least one analysis module, wherein the step of identifying comprises dividing said aqueous sample into a plurality of sub-samples and collecting information about each said sub-sample, wherein the step of collecting information about each said sub-sample comprises imaging any stainable structures in said particles in at least one sub-sample;
    and
    determining the geographic history of said target based on said identification of said at least one pollen particle.

2. The method of claim 1, wherein said step of collecting a sample of the particles from said target comprises swabbing said target to collect said particles and transferring said particles to an aqueous solution.

3. The method of claim 1, wherein said step of identifying the at least one particle in said sample comprises the step of:
    comparing said collected information to a database containing information about said at least one particle to identify said at least one particle.

4. The method of claim 3, wherein the step of comparing said collected information to a database containing information about said at least one particle to identify said at least one particle, comprises the steps of:
    compiling said collected information from each at least one sub-sample;
    retrieving identifying information from said database; and
    matching said identifying information to said collected information to identify said at least one particle in said aqueous sample.

5. The method of claim 4, wherein the step of determining the geographic history of said target based on said identification of said at least one particle comprises the steps of:
    cross-referencing the identity of each said at least one particle with a database containing geographic information about each said at least one particle; and
    calculating the geographic history of said target based on the geographic information of each said at least one particle identified in said aqueous sample.

6. The method of claim 1, further comprising the step of preparing a liquid sample of said collected sample by a sample preparation module.

7. The method of claim 6, further comprising the step of treating said liquid sample to isolate and purify DNA sequences contained therein by said sample preparation module.

8. The method of claim 7, wherein said step of identifying at least one pollen particle in said sample comprises the step of identifying the presence of at least one particular plant DNA sequence by performing a real time polymerase chain reaction on said isolated and purified DNA sequences.

9. The method of claim 8, wherein the step of determining further comprises the steps of:
    comparing said at least one particular plant DNA sequence with plant DNA sequence data stored in a database containing information about said plant DNA sequence data to identify said particular plant DNA sequence;
    matching said at least one particular plant DNA sequence with particular plant DNA sequence data stored in said database, wherein said particular plant DNA sequence data stored in said database is associated with known geographic distributions; and
    calculating the geographic history of said target based on the known geographic distributions of said at least one particular plant DNA sequence.

10. The method of claim 6, further comprising the step of treating said liquid sample to additionally stain for plant particles contained therein by said sample preparation module.

11. The method of claim 10, wherein said step of identifying the at least one particle in said sample further comprises the step of identifying the presence of at least one plant particle by performing an image analysis by an image analysis module and obtaining image analysis data of said at least one plant particle.

12. The method of claim 11, wherein the step of determining further comprises the steps of:
- comparing said image analysis data of said at least one plant particle with plant particle image analysis data stored in a database containing information about said plant particle image analysis data to identify said at least one plant particle;
- matching said image analysis data of said at least one plant particle with particular plant particle image analysis data stored in said database, wherein said particular plant particle image analysis data stored in said database is associated with known geographic distributions; and
- calculating the geographic history of said target based on the known geographic distributions of said at least one plant particle.

* * * * *